(12) United States Patent
Mak

(10) Patent No.: US 11,064,982 B2
(45) Date of Patent: *Jul. 20, 2021

(54) SYSTEMS, DEVICES AND METHODS FOR TISSUE REMOVAL AND ANALYSIS

(71) Applicant: SYNAPTIVE MEDICAL INC., Toronto (CA)

(72) Inventor: Siu Wai Jacky Mak, Toronto (CA)

(73) Assignee: SYNAPTIVE MEDICAL INC., Toronto (CA)

(*) Notice: Subject to any disclaimer, the term of this patent is extended or adjusted under 35 U.S.C. 154(b) by 770 days.

This patent is subject to a terminal disclaimer.

(21) Appl. No.: 15/862,915

(22) Filed: Jan. 5, 2018

(65) Prior Publication Data

US 2018/0125468 A1 May 10, 2018

Related U.S. Application Data

(63) Continuation of application No. 15/025,749, filed as application No. PCT/CA2015/050283 on Apr. 8, 2015, now Pat. No. 9,883,854.

(51) Int. Cl.
*A61B 10/02* (2006.01)
*A61B 5/1459* (2006.01)
(Continued)

(52) U.S. Cl.
CPC ........ *A61B 10/0283* (2013.01); *A61B 5/0066* (2013.01); *A61B 5/0075* (2013.01);
(Continued)

(58) Field of Classification Search
CPC ............ A61B 10/0283; A61B 18/1442; A61B 5/1455; A61B 5/0066; A61B 5/0075;
(Continued)

(56) References Cited

U.S. PATENT DOCUMENTS 4,622,974 A * 11/1986 Coleman ............... A61B 5/6848
356/440
6,564,087 B1 * 5/2003 Pitris ................... A61B 1/00172
600/478

(Continued)

OTHER PUBLICATIONS

Search Report issued by Intellectual Property Office of the UK in raltion to corresponding GB application No. GB1717752.8 dated Mar. 16, 2020; 5 pgs.

*Primary Examiner* — Rene T Towa

(57) ABSTRACT

Systems, devices and methods are provided for performing tissue removal and analysis based on the in-situ optical analysis of tissue and of liquid collected from the tissue region. In one example embodiment, a tissue removal and analysis probe includes an elongate tissue removal device, an optical fiber, and a fluid fillable conduit, where distal ends of the optical fiber and the conduit are in communication with an external region that is adjacent to a distal functional portion of the tissue removal device. The results of optical analysis one of both of external tissue and collected fluid may be employed to determine whether or not tissue removal is to be carried out. Various devices may be interfaced with the conduit for optical analysis of the collected fluid. In one example embodiment, the tissue removal device may be movable relative to the optical fiber and conduit.

16 Claims, 13 Drawing Sheets

(51) Int. Cl.
- *A61B 5/00* (2006.01)
- *A61B 5/1455* (2006.01)
- *A61B 5/1473* (2006.01)
- *A61B 5/1486* (2006.01)
- *A61B 18/14* (2006.01)
- *G01N 33/483* (2006.01)
- *A61B 90/00* (2016.01)
- *G01N 33/487* (2006.01)
- *G01N 21/65* (2006.01)
- *A61B 18/22* (2006.01)

(52) U.S. Cl.
CPC .......... *A61B 5/0084* (2013.01); *A61B 5/1455* (2013.01); *A61B 5/1459* (2013.01); *A61B 5/1473* (2013.01); *A61B 5/14552* (2013.01); *A61B 5/14865* (2013.01); *A61B 5/4887* (2013.01); *A61B 18/1442* (2013.01); *A61B 90/00* (2016.02); *G01N 21/658* (2013.01); *G01N 33/483* (2013.01); *G01N 33/487* (2013.01); *G01N 33/4833* (2013.01); *A61B 18/22* (2013.01)

(58) Field of Classification Search
CPC . A61B 5/0084; A61B 5/14552; A61B 5/1473; A61B 5/14865; A61B 5/4887; A61B 90/00; A61B 5/1459; A61B 15/22; A61B 1/00165; A61B 10/02; A61B 10/04; G01N 33/487; G01N 21/658; G01N 33/4833; G01N 33/483; G01N 21/4795; G01N 21/6486; G01N 21/65; G01N 2021/656

See application file for complete search history.

(56) References Cited

U.S. PATENT DOCUMENTS

2005/0259942 A1* 11/2005 Temelkuran ....... G02B 6/02385
385/147
2011/0112435 A1* 5/2011 Ramanujam ......... A61B 5/0071
600/567

* cited by examiner

SYSTEMS, DEVICES AND METHODS FOR TISSUE REMOVAL AND ANALYSIS

CROSS-REFERENCE TO RELATED APPLICATION(S)

This document is a continuation application which claims the benefit of, and priority to, U.S. patent application Ser. No. 15/025,749, filed on Mar. 29, 2016, entitled "SYSTEMS, DEVICES AND METHODS FOR TISSUE REMOVAL AND ANALYSIS" (now issued as U.S. Pat. No. 9,883,854, and International Patent Application No. PCT/CA2015/050283, filed on Apr. 8, 2015, entitled "SYSTEMS, DEVICES AND METHODS FOR TISSUE REMOVAL AND ANALYSIS," all of which are incorporated herein by reference in their entirety.

BACKGROUND

The present disclosure relates to optical tissue analysis devices. More particularly, the present disclosure relates to optical probes for intraoperative tissue analysis.

In current state-of-the-art neurosurgery, the main challenge in brain tumor removal lies in identifying and removing the brain tumor margins (i.e. the boundary between tumor tissue and heathy tissue) while not the damaging healthy brain tissue. However, identifying tumor margins accurately during surgery is deemed challenging. Tumor removal often relies on the experience of the surgeon in identifying the tumor and its margins. However, in order to avoid damaging and removing any healthy brain tissue, surgeons will only try to remove most of the tumor instead of removing more tissue than the identified tumor.

Recently, Raman spectroscopy has been demonstrated that it can identify brain tumor margins through detecting the unique, "fingerprint" like, chemistry signature from the tumors. However, these high resolution, high power, and highly sensitive Raman spectrometer, or Raman system, are not stable and ergonomic enough to be used in an operation room environment. The design of these Raman systems also requires the tissue to be placed in close proximity (<1 cm) to the optical detection port to achieve a strong detected Raman signal from the tissue. This is difficult for open surgery if the tissue of interest is far away from the top of the opening. In non-open surgery, such as port-based surgeries, this design is not practical to be used in the operation room.

Some Raman systems, with lower resolution, lower power or lower sensitivity, can be used to identify tumor and tumor margin. These Raman systems require a long integration time (>1 min) to obtain a sufficiently strong Raman signal from the tissue to enables differentiation between healthy and tumor signatures. To differentiate between endogenous Raman signatures of healthy tissue and tumor tissue, statistic techniques may be used. Nevertheless, the accuracy of such approaches is constrained by difficulties in detecting a clear difference in the Raman spectra between healthy tissue and tumor tissue.

SUMMARY

Systems, devices and methods are provided for performing tissue removal and analysis based on the in-situ optical analysis of tissue and of liquid collected from the tissue region. In one example embodiment, a tissue removal and analysis probe includes an elongate tissue removal device, an optical fiber, and a fluid fillable conduit, where distal ends of the optical fiber and the conduit are in communication with an external region that is adjacent to a distal functional portion of the tissue removal device. The results of optical analysis one of both of external tissue and collected fluid may be employed to determine whether or not tissue removal is to be carried out. Various devices may be interfaced with the conduit for optical analysis of the collected fluid. In one example embodiment, the tissue removal device may be movable relative to the optical fiber and conduit.

Accordingly, in a first aspect, there is provided a tissue removal and analysis system comprising:
 a tissue removal and analysis probe comprising:
  an elongate tissue removal device having a distal portion that is configured to sample or remove tissue;
  an optical fiber having a distal end in optical communication with an external region that is adjacent to said distal portion; and
  a fluid-fillable conduit having a distal aperture in fluid communication with the external region for collecting a fluid sample from the external region; and
 an optical detection subsystem configured to be in optical communication with a proximal end of said optical fiber and with at least a portion of the fluid sample collected by said fluid-fillable conduit;
 wherein said optical detection subsystem is configured to direct first incident optical energy into said optical fiber and to detect first received optical energy that is responsively produced within the external region; and
 wherein said optical detection subsystem is further configured to direct second incident optical energy into the fluid sample collected by said fluid-fillable conduit, and to detect second received optical energy that is responsively produced within the fluid sample.

In another aspect, there is provided a tissue removal and optical detection probe comprising:
 an elongate tissue removal device having a distal portion that is configured to sample or remove tissue;
 an optical fiber having a distal end in optical communication with an external region that is adjacent to said distal portion; and
 a fluid-fillable conduit having a distal aperture in fluid communication with the external region for collecting a fluid sample from the external region;
 wherein said fluid-fillable conduit is configured to be connectable to an optical detection subsystem, such that the fluid sample collected in said fluid-fillable conduit is in optical communication with said optical detection subsystem when said fluid-fillable conduit is connected to said optical detection subsystem.

In another aspect, there is provided a method of performing tissue removal based on optical tissue analysis, the method comprising:
 positioning the distal portion of a tissue removal and analysis probe adjacent to a tissue region;
 collecting, within the conduit, fluid from the tissue region;
 direct first incident optical energy into the optical fiber and detecting first received optical energy that is responsively produced within the tissue region, thereby obtaining first received signals; and
 directing second incident optical energy into the fluid collected by the fluid-fillable conduit, and detecting second received optical energy that is responsively produced within the fluid sample, thereby obtaining second received signals;
 processing the first received signals and the second received signals to determine whether one more pre-selected criteria are met; and in the event that the one or more criteria are satisfied, employing the tissue removal device to perform tissue removal.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
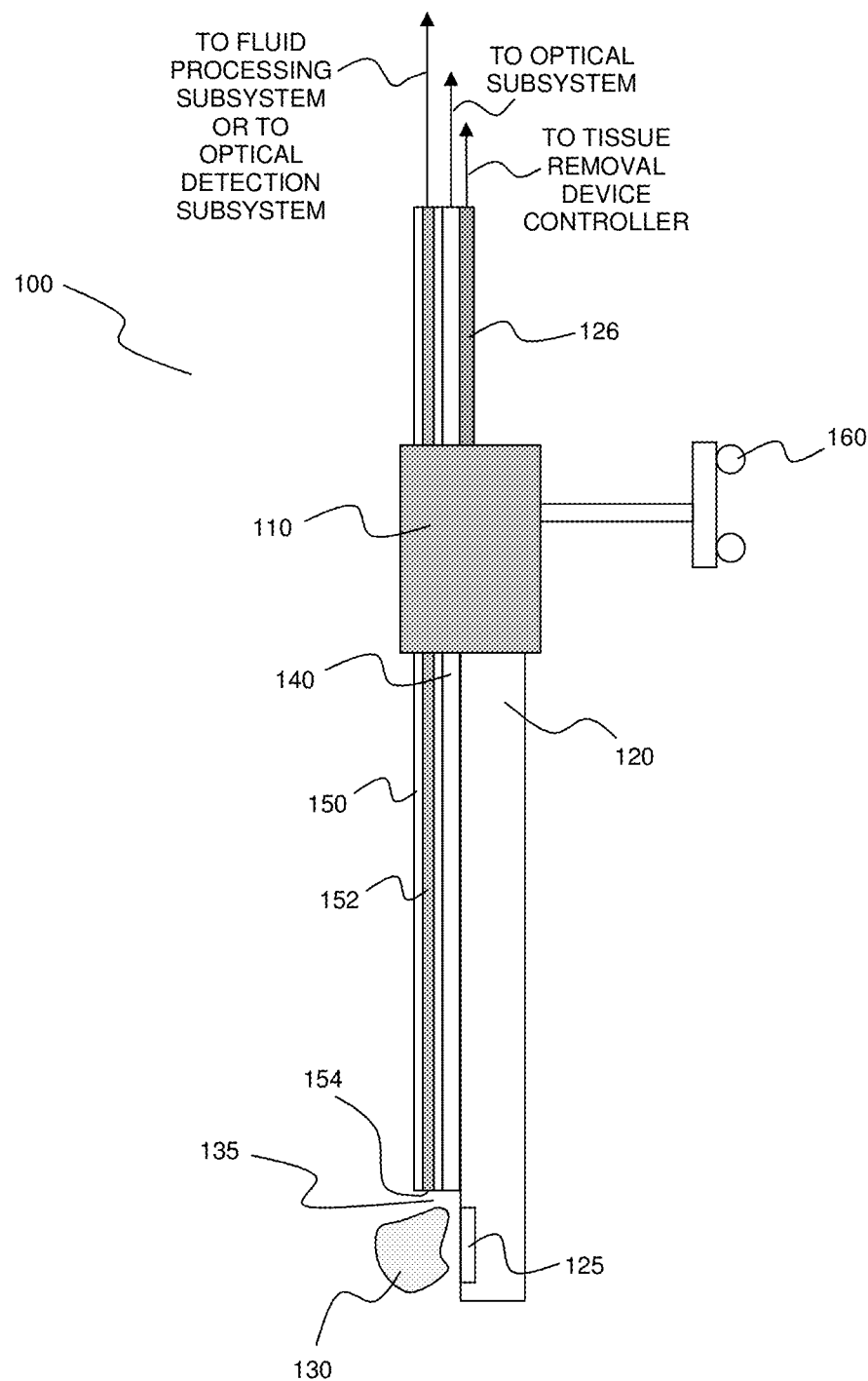
FIG. 1 shows an example tissue removal and analysis device.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein, the term "fluid" refers to liquid and/or gaseous substances.

In various example embodiments of the present disclosure, systems, device and methods are provide that enable the optical interrogation of both solid tissue and fluid samples within a region of interest, thereby allowing the optical interrogation of fluid that resides at or near tissue of interest.

The optical analysis of localized fluid collected from a region of interest, in addition to the optical analysis of the tissue within the region of interest, may be beneficial providing in identifying tumor margins more accurately. For example, in tumor/tumor margin identification using statistical analysis methods (i.e. principle component analysis), Raman spectra from both the tissue and its local extracellular, inter-cellular and intra-cellular fluid/matrix can be obtained together to potentially improve the accuracy in tumor identification. Accordingly, various embodiments of the present disclosure, and variations thereof, may be beneficial in improving the detection of endogenous contrast in tissue based on the additional optical data and analysis afforded by the collection of fluid samples from the region of interest.

Referring now FIG. 1, an example embodiment of an tissue removal and analysis probe 100 is illustrated, in which probe 100 is adapted for the optical interrogation of a tissue within a region of interest residing external to a distal region of the device, and where the probe is also configured for the collection, and optical interrogation, of a fluid sample collected from the region of interest. Example tissue removal and analysis probe 100 includes a body portion 110 that is configured to be manually or robotically supported, where the body portion 110 houses, or mechanically supports, a tissue removal device 120.

As shown in FIG. 1, a distal tissue removal portion 125 of tissue removal device 120 is configured to sample or remove tissue 130. Examples of suitable tissue removal devices are described below.

Probe 100 also includes an optical fiber 140 having a distal end in optical communication with an external region 135 that is adjacent to distal tissue removal portion 125 of tissue removal device 120. Optical fiber 140 may be connected, other otherwise brought into optical communication, with an optical detection system, for optically interrogating tissue 130.

A fluid-fillable conduit 150, having a lumen 152 a distal aperture 154 in fluid communication with the external region 135, is provided for collecting a fluid sample from the external region 135. The fluid fillable conduit 150 may be configured to collect the fluid sample passively (e.g. via capillary action) or under the control of an active fluidic device, such as a pump. Various example configurations of the interfacing of fluidic devices with fluid-fillable conduit 150 are described below. As shown in FIG. 1, conduit 150 may be directly interfaced with an optical detection system (for the optical interrogation of fluid collected within lumen 152), or conduit 150 may be indirectly interfaced with an optical detection system via a fluid processing subsystem.

Optical fiber 140 and fluid conduit 150 may be provided within a common longitudinal housing. In some example implementations, the distal end of optical fiber 140 and distal aperture 154 of conduit 150 are separated by a distance of less than 1 cm, less than 5 mm, less than 2.5 mm, less than 1 mm, or less than 500 microns. In some example implementations, the distal end of optical fiber 140 and/or distal aperture 154 of conduit 150 are separated from distal tissue removal portion 125 of tissue sampling device 120 by a distance of less than 1 cm, less than 5 mm, less than 2.5 mm, less than 1 mm, or less than 500 microns.

Although optical fiber 140 and conduit 150 are shown as extending from body portion 110 in a continuous, uninterrupted manner, for interfacing with external subsystems, it will be understood that optical fiber 140 and/or conduit may connect with a respective optical fiber or conduit via a connector provided in a proximal region of probe 100 (e.g. within body potion 110). Tissue removal device 120 may be connected to an external controller (or suitable computing device) via cable 126, or alternatively, via a wireless connection.

As also shown in FIG. 1, example tissue resection and optical analysis probe may have one or more fiducial markers 160 attached thereto. For example, fiducial markers 160, tracked via a tracking system, may be employed in order to determine the real-time (e.g. intraoperative) location of probe 100. For example, the tracked fiducial markers 160 may be employed to track the location of one or more functional locations of probe 100 (e.g. the distal end of optical fiber 140, the distal aperture 154 of conduit 150, and/or the distal tissue removal portion 125 of tissue removal device 120). Such tracking may be useful in correlating or registering the locations of optical measurements with measurements made using other imaging or detection modalities (e.g. including, but not limited to, magnetic resonance imaging, optical coherence tomography, ultrasound, near infrared imaging, hyperspectral imaging) through intra-surgical tracking and registration.

Figure 2:
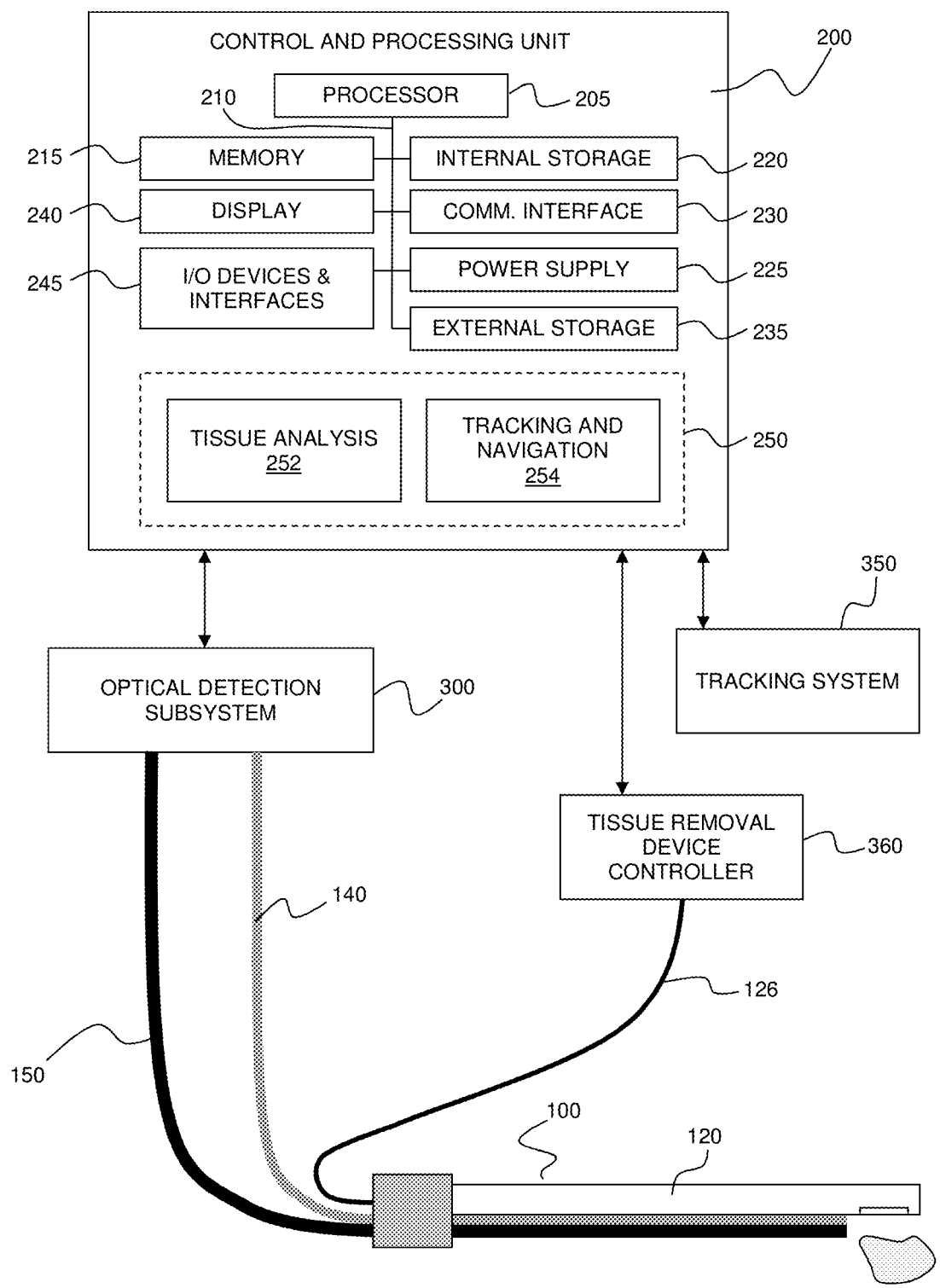
FIG. 2 shows an example system for performing tissue removal and optical analysis.

Referring now to FIG. 2, an example system is shown, whereby tissue removal and analysis probe 100 is interfaced with a plurality of subsystems. The example system includes tissue removal and analysis probe 100, optical detection subsystem 300, tracking system 350, tissue removal device controller 360, and control and processing unit 200. The spatial position and orientation of the tissue removal and analysis probe 100 may be monitored by tracking system 350, as noted above.

FIG. 2 provides an example implementation of control and processing unit 200, which includes one or more processors 205 (for example, a CPU/microprocessor or a graphical processing unit, or a combination of a central processing unit or graphical processing unit), bus 210, memory 215, which may include random access memory (RAM) and/or read only memory (ROM), one or more internal storage devices 220 (e.g. a hard disk drive, compact disk drive or internal flash memory), a power supply 225, one more communications interfaces 230, optional external storage 235, optional display 240 and one or more input/output devices and/or interfaces 245 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a foot switch, and/or a microphone for capturing speech commands).

Control and processing unit 200 may be programmed with programs, subroutines, applications or modules 250, which include executable instructions, which when executed by the processor, causes the system to perform one or more methods described in the disclosure. Such instructions may be stored, for example, in memory 215 and/or internal storage 220. In particular, in the example embodiment shown, tissue analysis module 252 includes computer executable instructions for analyzing optical data obtained from optical detection system. For example, computer readable instructions may be provided for processing optical data obtained at different spatial locations in order to determine the location of a tumor margin based on endogenous tissue contrast. The spatial location may be correlated with the recorded optical data via the tracking of the position and orientation of tissue removal and analysis probe 100. The example modules 250 shown in FIG. 2 also include tracking and navigation module 254, which may include executable instructions for processing tracking data, and/or for rendering a navigation user interface on a display. It will be understood that the example processing modules shown in FIG. 2 are provided merely as non-limiting, illustrative examples.

Although only one of each component is illustrated in FIG. 2, any number of each component can be included in the control and processing unit 200. For example, a computer typically contains a number of different data storage media. Furthermore, although bus 210 is depicted as a single connection between all of the components, it will be appreciated that the bus 210 may represent one or more circuits, devices or communication channels which link two or more of the components. For example, in personal computers, bus 210 often includes or is a motherboard. Control and processing unit 200 may include many more or less components than those shown. It is also noted that one or more external subsystems, such as tissue removal device controller 126, may instead be integrated directly within control and processing unit 200.

In one embodiment, control and processing unit 200 may be, or include, a general purpose computer or any other hardware equivalents. Control and processing unit 200 may also be implemented as one or more physical devices that are coupled to processor 205 through one of more communications channels or interfaces. For example, control and processing unit 200 can be implemented using application specific integrated circuits (ASICs). Alternatively, control and processing unit 200 can be implemented as a combination of hardware and software, where the software is loaded into the processor from the memory or over a network connection.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refers to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

As shown in FIG. 2, optical fiber 140 may be directly interfaced with optical detection subsystem 300, such that optical excitation energy from optical detection subsystem 300 is coupled into optical fiber 140 for delivery and excitation of tissue external to tissue removal and analysis probe 100, and such that optical energy that is responsively generated within the tissue and collected by optical fiber 140 is delivered to, and detected by, optical detection subsystem 300.

Optical detection system 300 is also configured to optically interrogate fluid that is collected by within conduit 150. The optical coupling of optical detection system with the fluid collected by conduit 150 may be achieved according to many different embodiments. The configuration shown in FIG. 2 illustrates but one example coupling configuration, in which a proximal end of conduit 150 is interfaced with optical detection subsystem, such that optical excitation energy may be directly coupled to the fluid collected within the proximal portion of conduit 150. In the example configuration shown in FIG. 2, the fluid may fill the conduit under capillary action (i.e. lumen 152 may be sufficiently small to draw fluid from the external region adjacent to the tissue to optical detection subsystem 300). Optical detection subsystem 300 may alternatively include a mechanism for generating a negative pressure relative to distal aperture 154, such that fluid is actively drawn.

In the example embodiment shown in FIG. 2, optical detection subsystem 300 is configured to couple optical excitation energy into the fluid collected within fluid conduit 150, and to detect optical energy that is responsively emitted from the fluid. Various non-limiting example configurations for coupling the optical energy into the fluid within conduit 150 are shown in FIGS. 3A-3E.

Figure 3A:
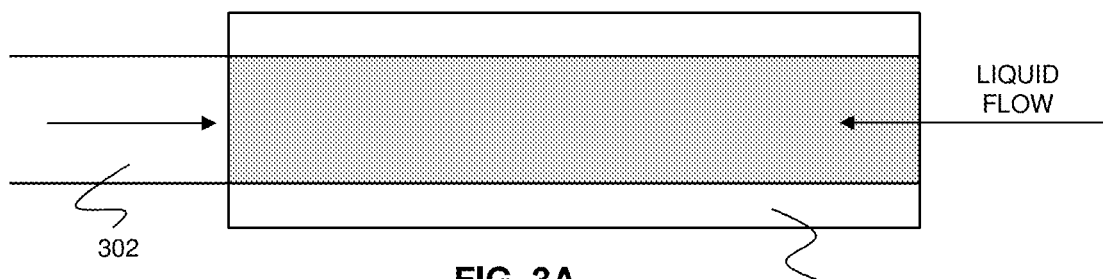
FIGS. 3A-E show non-limiting example configurations for coupling optical energy into the fluid within the conduit 150.

In FIG. 3A, an example implementation is shown in which an external optical fiber 302 (e.g. a fiber housed within optical detection subsystem 300) is brought into contact (butt coupling) with the fluid collected within conduit 150. As noted above, the fluid may be drawn into the conduit passively (e.g. via capillary forces), or actively, such as via a pressure reduction mechanism (e.g. a fluid pump or a vacuum).

Figure 3B:
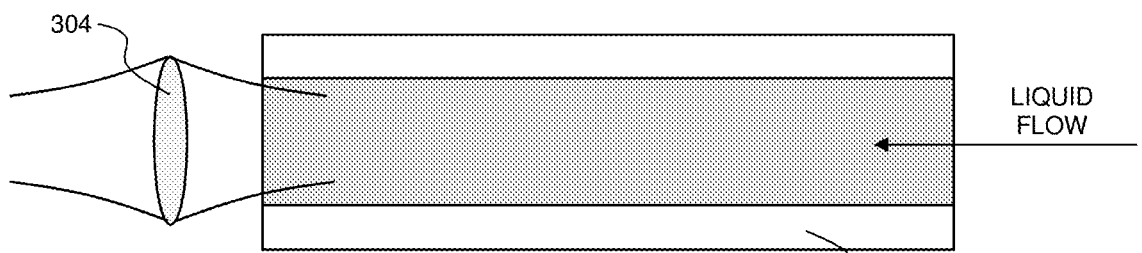

FIG. 3B illustrates a second example implementation in which the optical energy is coupled through free space into the fluid within conduit 150 using a focusing element. Although FIG. 3B shows a specific example embodiment involving lens 304, it will be understood that any suitable optical element may be employed for coupling of the light, such as, but not limited to, a lens, mirror, a diffractive element. The configuration shown in FIG. 3B is also schematically illustrated in FIG. 3E, where fluid flows into the distal end of conduit 150, and is optically interrogated at the proximal end thereof.

Figure 3C:
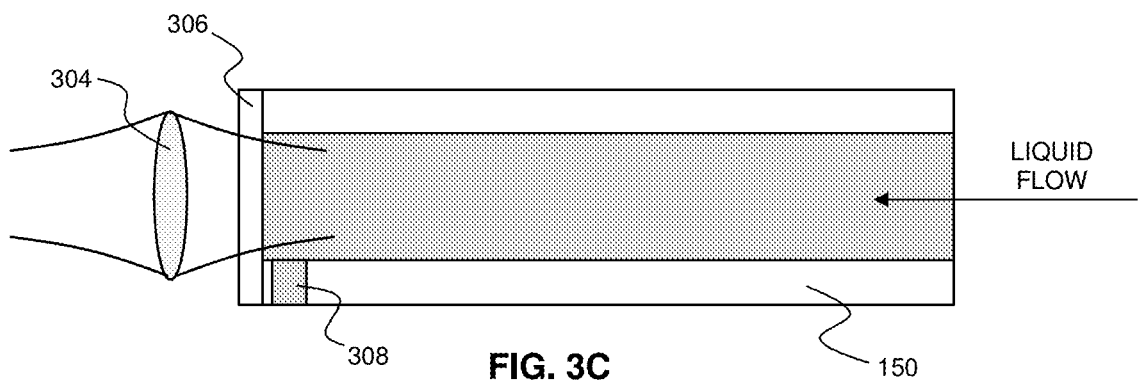
Figure 3D:
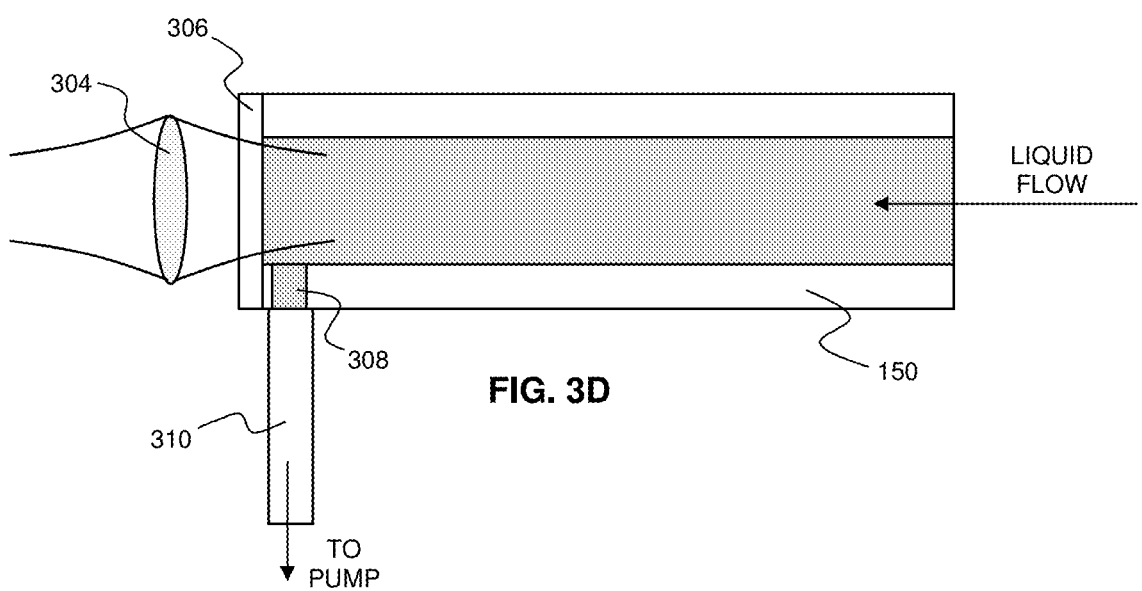
Figure 3E:
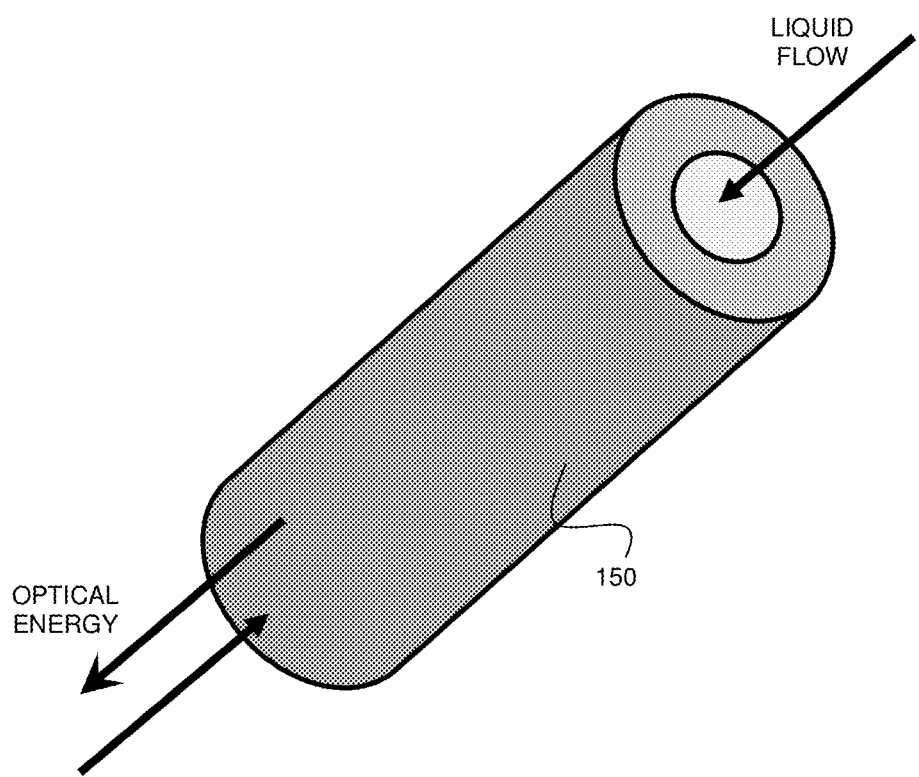

In the configuration shown in FIG. 3B, the optical energy is shown as being directly coupled into the fluid. FIG. 3C illustrates an alternative example implementation in which a proximal end of conduit 150 is closed. In the example implementation shown in the figure, the proximal end is closed (e.g. enclosed or capped) by an optical window 306. As shown in the figure, a lateral port 308 enables filling of the fluid within the conduit, such that the fluid contacts window 306. Although FIG. 3C shows the coupling of light into the fluid through free space via a focusing element, it will be understood that the optical energy may be coupled through window 306 in a fiber-based, butt coupled configuration, such as that shown in FIG. 3A.

As noted above, the fluid may be drawn into the conduit passively (e.g. via capillary forces), or actively, such as via a pressure reduction mechanism (e.g. a fluid pump or a vacuum). In the example implementation shown in FIG. 3D, a lateral conduit 310 is shown that connects, or is connectable, to an external pump of vacuum generating mechanism.

Figure 4:
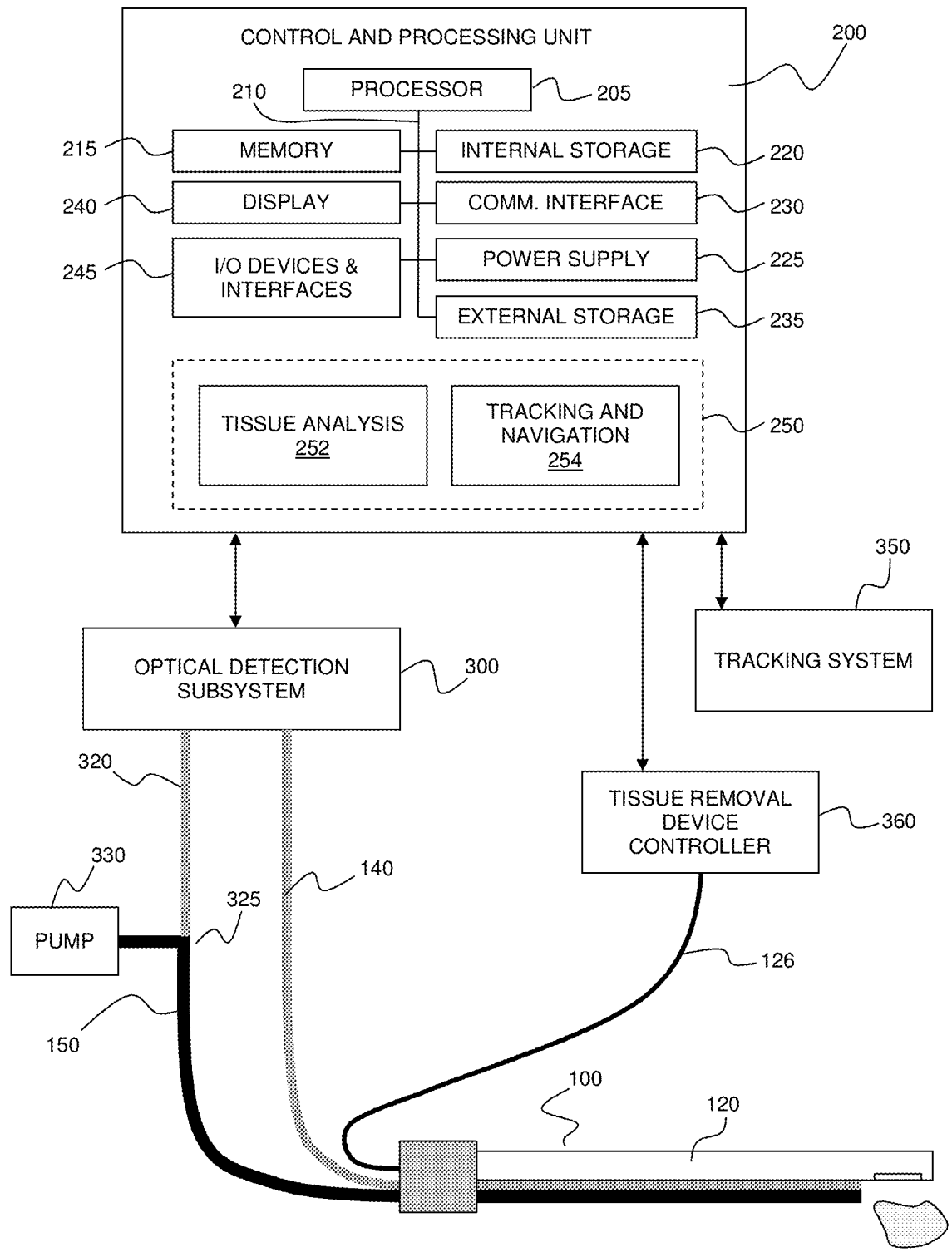
FIG. 4 shows another example system for performing tissue removal and optical analysis, in which an external pump is employed to collected fluid within the conduit.

As described above, in the example system shown in FIG. 2, fluid conduit 150 is interfaced with optical detection subsystem 300. In an alternative example implementation, the fluid conduit may be interfaced with an external optical fiber at an intermediate location external to optical detection system 300. An example of such a configuration is shown in the system illustrated in FIG. 4, in which external optical fiber 320 extends from optical detection subsystem 300 to an intermediate location 325, where a distal end of external optical fiber 320 is brought into optical communication with fluid collected within conduit 150. The example configuration shown in FIG. 4 may be implemented, for example, using an optical-fluid coupling arrangement similar to that illustrated in FIG. 3D (optionally by butt coupling the distal end of external optical fiber 320 to window 306), and employing pump 330 to draw fluid into conduit 150 from the external region.

Figure 5A:
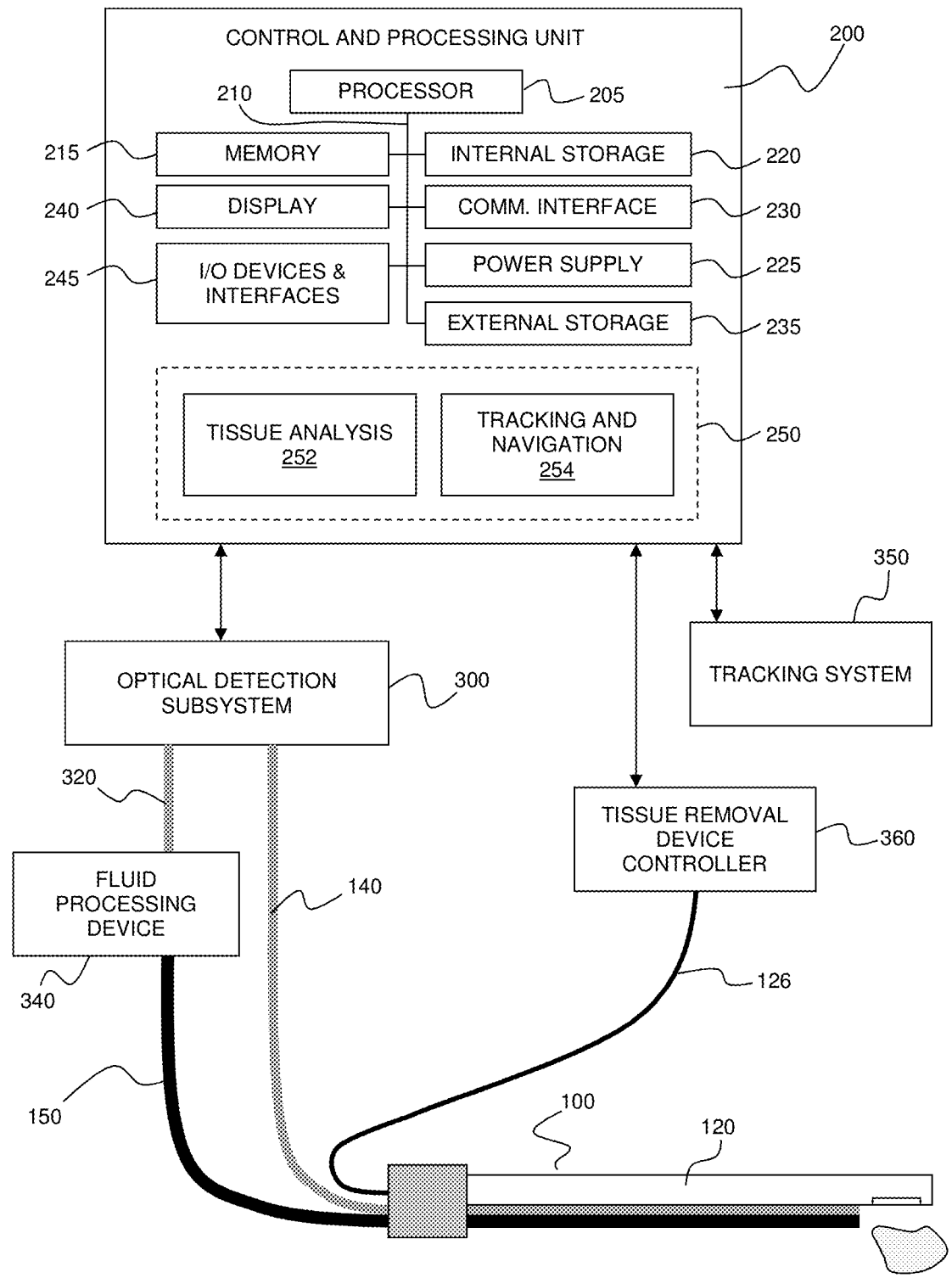
FIG. 5A shows another example system for performing tissue removal and optical analysis in which the fluid conduit is interfaced with a fluid processing device.
Figure 5B:
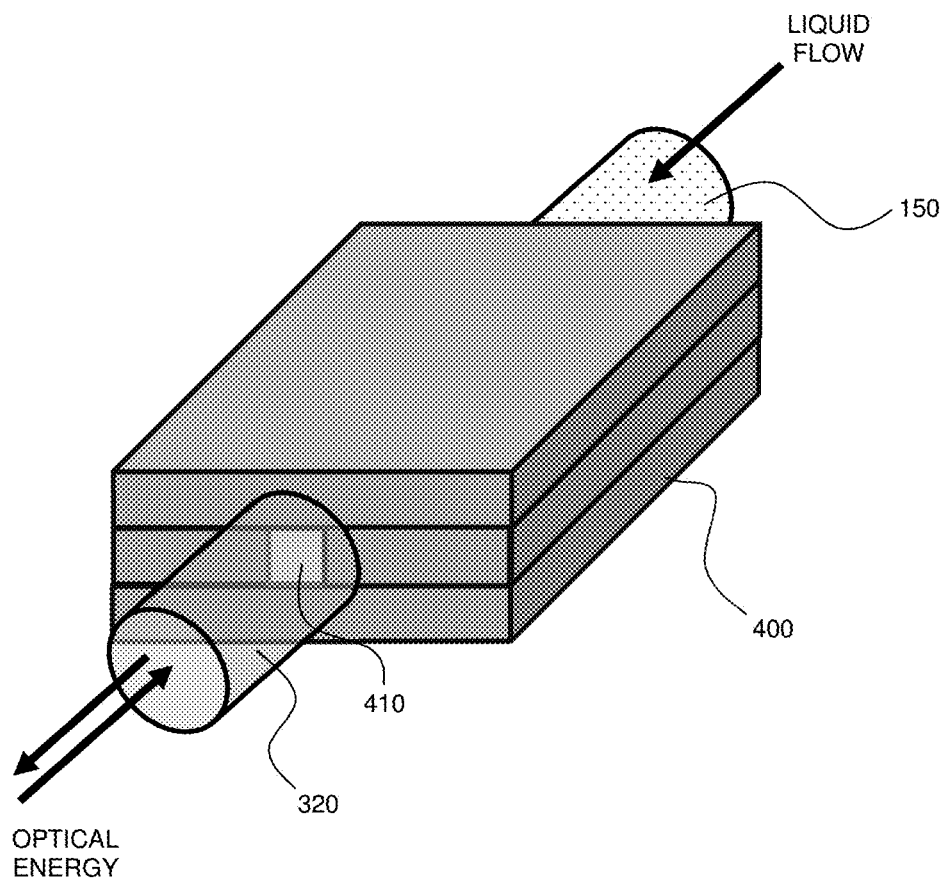
FIG. 5B is an illustration the interfacing of an example microfluidic device with a conduit and an optical fiber.

FIG. 5A illustrates another non-limiting example system in which a fluidic processing device 340 is employed to pre-process the collected fluid before it is brought into optical communication with optical detection system 300. In one example embodiment, fluidic processing device 340 may be a microfluidic device, such as a device comprising one or more channels with a spatial dimension less than approximately 1 mm, or a device configured to process fluid volumes less than approximately 1 milliliter. FIG. 5B illustrates an example implementation in which external optical fiber 320 is shown as being interfaced with microfluidic device 400, such that the core of optical fiber 320 is brought into optical communication with an internal flow channel 410 within microfluidic device 400. Microfluidic device may be formed with transparent materials having indices of refraction such that internal flow channel 410 acts an optical waveguide when filled with fluid (e.g. via total internal reflection or Bragg reflection). Microfluidic device 400 may be interfaced with an external pump or vacuum generating device such that fluid is drawn into conduit 150 and transported to microfluidic device 400.

Microfluidic device 400 may include one or more functional regions configured to process the collected fluid before the collected fluid is optically interrogated with optical energy delivered by external optical fiber 320. For example, whole blood from the brain could be collected by conduit 150 and delivered to microfluidic device 400, where a microfluidic extraction protocol could be performed to separate one or more constituents of interest, such as cells or macromolecules before an analytical interrogation step is performed. Such fluidic pre-processing of the collected fluid sample may be advantageous in increases the accuracy or sensitivity of the subsequent optical analysis.

In one non-limiting example implementation, microfluidic device 400 may be configured to perform separation, whereby microfluidic device 400 includes a separation mechanism, such as, but not limited to, a filter, a filtration obstacle region, separation media, a magnetic separation chamber, a flow cytometric region, an electrophoretic separation region, and a dielectrophoresis separation region. Microfluidic device 400 may additionally or alternatively be configured to perform an assay, such as an assay involving an optical label such as a fluorescent label, or a label-free assay. Other non-limiting examples of microfluidic components that may be included for the pre-processing of the collected fluid include lysis chambers (e.g. employing one or more of bead based mechanical lysis, electrical lysis, and ultrasonic lysis mechanisms).

In some embodiments, the fluid conduit, or at least a portion thereof, may be configured to support the internal guidance of optical energy when the conduit lumen is filled with collected fluid. In other words, at least a portion of the conduit may be configured as an optical waveguide, such that optical excitation energy that is coupled into a proximal end of the conduit propagates within the lumen of the conduit. The fluid conduit, or at least a portion of the fluid conduit, may therefore be a hollow-core optical fiber that provides lateral confinement and guiding of optical energy within the fluid-filled core.

Such an embodiment may be advantageous in facilitating a longer interaction length between the optical excitation energy and the fluid collected within the lumen, which may provide an enhancement in signal and detected endogenous contrast. Furthermore, in some embodiments, the lumen of the conduit may be configured to have a diameter that is sufficiently small to promote and/or enhance nonlinear optical interactions. For example, in some example embodiments, a portion of the fluid conduit that is configured as an optical waveguide (when filled with the collected fluid) may have a diameter less than 100 microns, less than 50 microns, less than 25 microns, less than 20 microns, less than 15 microns, less than 10 microns, or less than 5 microns.

For example, the lateral confinement of the optical excitation energy may be employed to facilitate the production of an increased Raman signal. In this technique, fluid sample of interest is filled into the core of a hollow-core fiber from the distal end of the hollow-core fiber. In the opposite end, light is confined in the radial direction and propagating through the fluid core along the length of the fiber. The input light will then interact with the fluid in the core and induce Raman scattering over the propagation length of the optical excitation energy. In some embodiments, this propagation length may be only a portion of the total length of the hollow-core fiber, due to scattering and/or absorption. In other example embodiments in which the optical excitation energy is not substantially attenuated within the fluid core, the interaction may occur throughout the entire length of the hollow-core fiber. Due to the interaction of the optical excitation energy with the fluid, an induced Raman signal is produced via Raman scattering. This signal is also confined within the fiber core, and propagates towards the proximal end of the conduit, where is it optically delivered to the optical detection system for detection and subsequent processing and analysis. Using such a technique, the detected Raman signal may be increased by approximately two orders of magnitude relative to using a conventional technique that employs an objective for coupling the optical excitation energy without subsequent optical internal confinement and guidance within the conduit. Since Raman scattering signal is induced between the laser and the sample inside the hollow-core fiber, more Raman scattering signal may also be generated with a prolonged fiber length (depending on the relative attenuation of the optical excitation beam).

It will be understood that the optical energy may be confined and guided according to several different mechanisms. In one example implementation, the walls of the fluid conduit are selected to have a lower refractive index the fluid-filled core, such that the optical energy is guided via total internal reflection. Examples of such hollow-core optical fibers include hollow core polymer fibers, and Teflon capillary tubes.

In other example embodiments, the optical energy may be guided via a mechanism other than total internal reflection. For example, the conduit, or at least a portion thereof, may be, or may include, a photonic crystal fiber, photonic bandgap fiber, whereby Bragg reflection or multiple interferences are employed to achieve confinement. As the air holes of such fibers are typically a few microns in diameter, the volume of fluid required to fill the core of the entire fiber length is only typically only nanoliters to microliters. Accordingly, only a very small sample of fluid is required from a local region to increase the endogenous Raman signal differences between tumor and healthy tissue.

Referring again to FIGS. 2, 4 and 5A, it will be understood that optical detection subsystem 300 generally includes at least one optical source (e.g. a laser, light emitting diode, or other optical source known in the art) and at least one optical detector. One source may be optically coupled to both of optical fiber 140 and the fluid collected within conduit 150 (e.g. using a beamsplitter), or alternatively, separate sources may be employed. Similarly, a detector may be shared for detection of optical energy collected from optical fiber 140 and from the fluid within conduit 150 (e.g. using a beamsplitter, with a removable beam block on one of both channels to select a single channel for detection), or separate detectors may be employed. The choice of a suitable detector will depend on a number of factors, including the type of optical modality that is employed for fluid and tissue analysis. Furthermore, in some embodiments, the collected optical energy that is received from one or both of optical fiber 140 and from the fluid within conduit 150 may be spectrally resolved using a spectrometer (or other spectrally selective optical element or optical device) prior to detection.

Optical detection system 300 may be employ any one or more of a wide variety of optical modalities, including, but not limited to, Raman, fluorescence and reflectance modalities. In some example embodiments, the optical detection system may include one or more optical spectrometers.

In some embodiments, a common optical modality may be employed for tissue detection (via optical fiber 140) and for fluid optical analysis (via conduit 150). For example, both tissue and fluid optical analysis may be performed via optical fluorescence detection or Raman detection. In one example implementation, the optical detection subsystem 300 is configured for the excitation and detection of Raman signals in an external region via optical fiber 140, and for the excitation and detection of Raman signals from fluid that collected within conduit 150. Such an example embodiment may be employed to detect Raman signals from solid samples, such as tissue, as well as from localized fluidic samples, such as blood, protein, inter-cellular fluid and intra-cellular fluid.

Figure 6A:
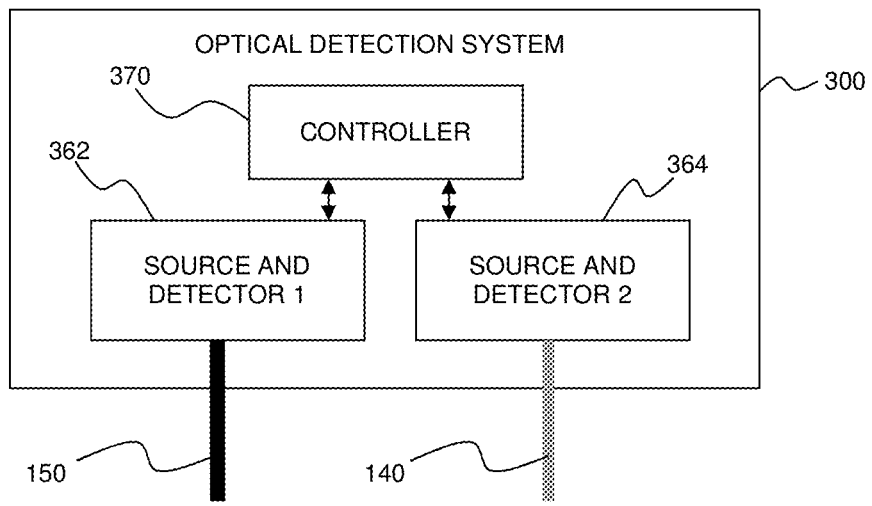
FIGS. 6A and 6B illustrate example implementations of an optical detection subsystem.
Figure 6B:
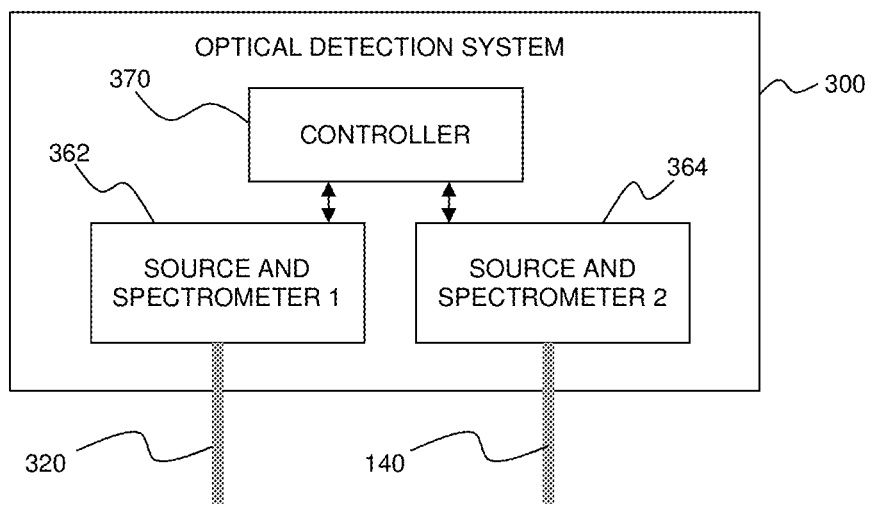

FIGS. 6A and 6B schematically show two different configurations of optical detection subsystem 300. In FIG. 6A, optical detection system is shown interfaced with fluid filled conduit 150, as described above with reference to FIGS. 2 and 3A-E. Dedicated sources and detectors 362 and 364 are separately interfaced with the fluid collected in conduit 150 and with optical fiber 140, respectively, for optical fluid analysis and optical tissue analysis, respectively. As noted above, one or both of sources and detectors 362 and 364 may include a spectrometer or one or more spectrally selective optical components. Controller 370, which may include one or more processors, memory elements, and/or other computing components (e.g. any of those illustrated in control and processing unit 200), is employed to control one or more functions of source/detectors 362 and 364, and is interfaced with control and processing unit 200. Controller 370 may also or alternatively provide at least some processing of the received signals. FIG. 6B illustrates an alternative configuration in which optical detection system 300 is shown indirectly interfaced with the fluid filled conduit via external optical fiber 320, as described with reference to FIG. 4.

Figure 6C:
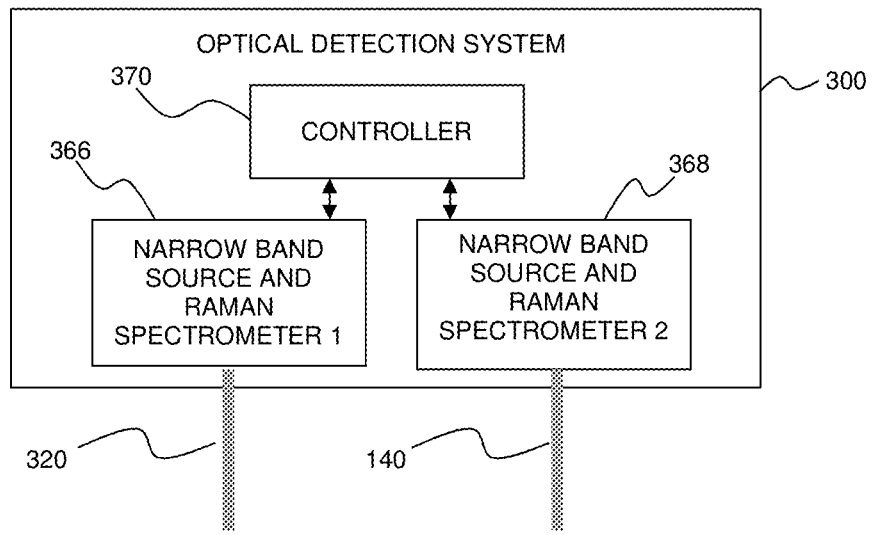
FIG. 6C is an illustration of an example optical detection subsystem that employs Raman detection.

Referring now to FIG. 6C, an example implementation of an optical detection subsystem for Raman detection is illustrated. The implementation is similar to FIG. 6B in which it consists of two sources and two spectrometers and a controller that controls the sources and spectrometers. Dedicated sources and detectors 366 and 368 are separately interfaced with the fluid filled conduit via external optical fiber 320 and with optical fiber 140, respectively, for optical fluid analysis and optical tissue analysis, respectively.

For Raman detection, a narrowband source and spectrometer for narrower band dispersion is used for detecting the Raman scattering signals. Typically, source for Raman detection has a 3 dB bandwidth of around 0.03 nm, center wavelength stable within 0.1 nm and power stability of <5%. A typical Raman spectrometer covers a range of about 785-1200 nm for Stokes Raman detection with an excitation at 785 nm and 633-790 nm for Stokes Raman detection with an excitation at 633 nm.

Figure 6D:
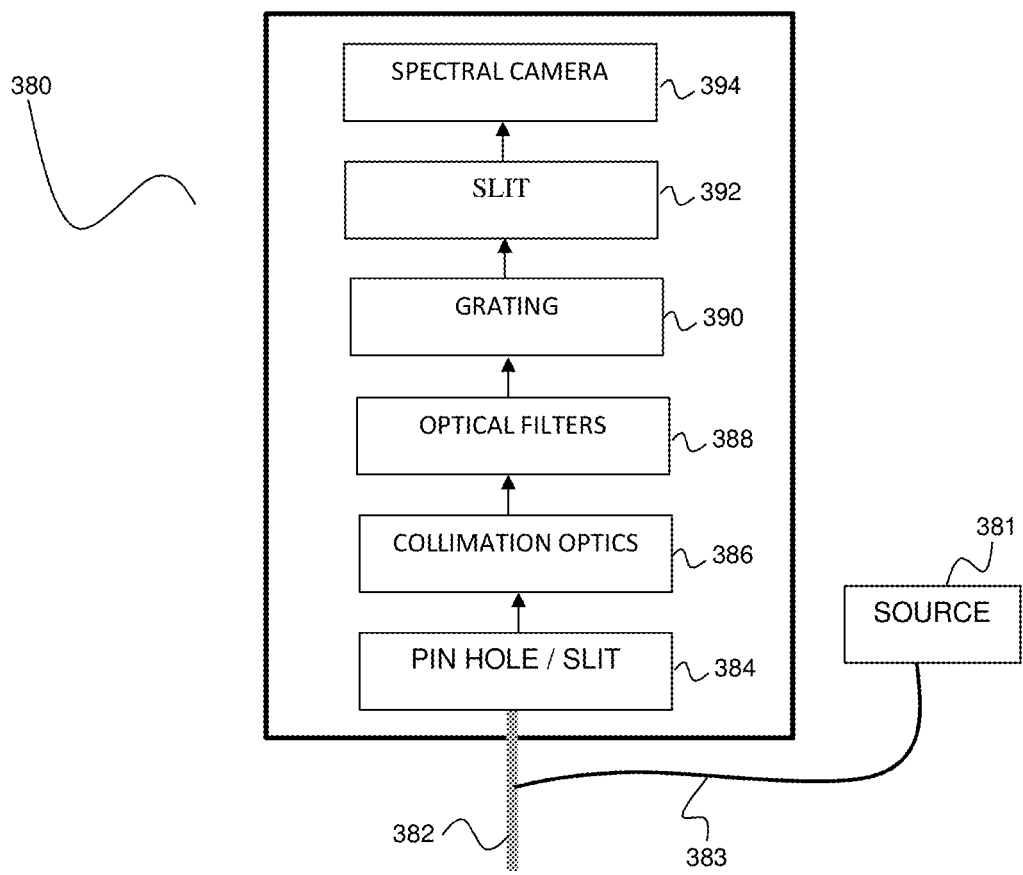
FIG. 6D is an illustration of an example optical detection subsystem that employs Raman detection, showing various example internal components.

FIG. 6D shows an example configuration of a Raman spectrometer 380 with an excitation source 381. This configuration utilizes a fiber bundle 382 that splits at least one optical fiber 383 to source 381. Source 381 excites the sample through fiber bundle 382. The rest of the fibers in bundle 382 collect the scattering signals from the sample and direct it to a pin hole or slit 384 for controlling the spatial resolution and light collection. The pass through light is then collimated 386 and passes through an optical filter 388 to filter out the excitation light and let only the Raman scattering signal to pass through. The Raman scattering light is then spatially spread out using a grating 390 to cover the spectral camera sensing chip 394 through another optional slit 392.

In other embodiments, different optical modalities may be used for tissue detection (via optical fiber 140) and for fluid detection (via conduit 150). For example, fluorescence detection may be employed for tissue analysis, and Raman spectroscopy may be employed for fluid analysis, or vice versa. In other embodiments, optical detection system may be a multimodal system that is reconfigurable such that one of a plurality of optical modalities may be selectively employed for one of both of tissue analysis and fluid analysis.

Referring again to FIG. 1, it will be understood that tissue removal device 120 may be any device that is capable of the removal, sampling, or resection of tissue, such as, but not limited to, tissue resection devices, tissue ablation devices, and tissue biopsy devices. It will also be understood that the configuration of the probe will depend on the specific tissue removal device that is employed. For example, although FIG. 1 shows an elongate tissue removal device, supported by body portion 110, with adjacent optical fiber 140 and fluid conduit 150, this configuration is but one example configuration. For example, in another example implementation, one or more of tissue removal device 120, optical fiber 140, and fluid conduit 150 may be housed within an elongate body (optionally with a removable sheath), provided that the distal portions thereof are accessible to the external region.

Figure 7:
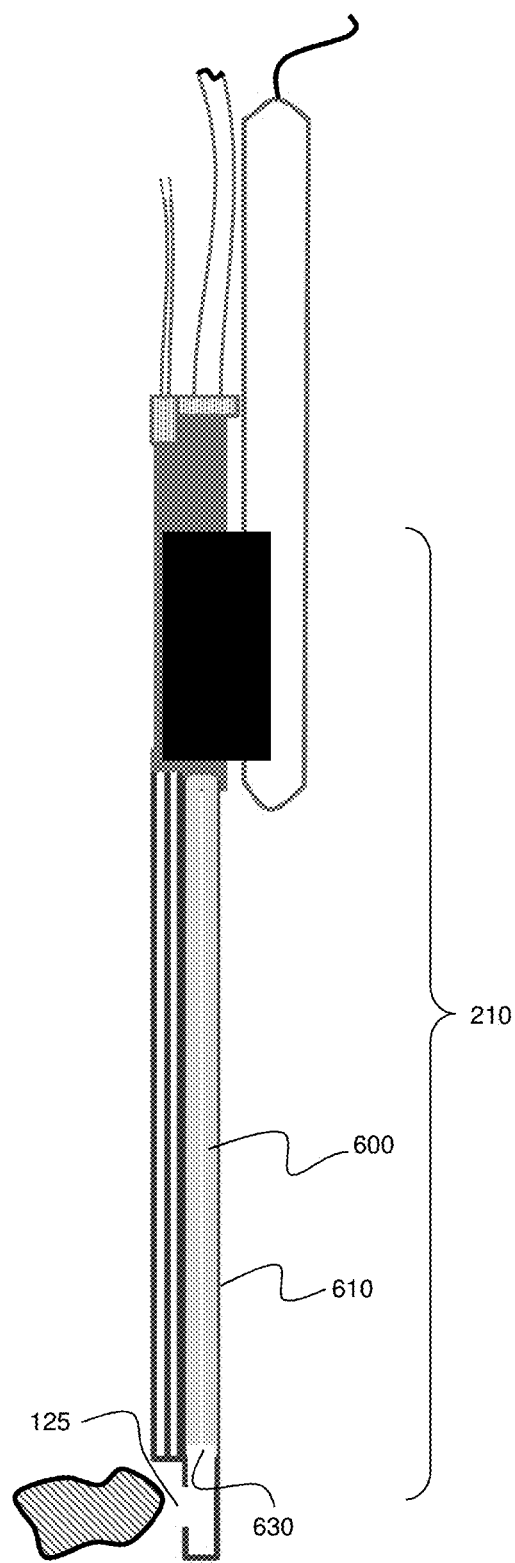
FIG. 7 is an illustration of an example tissue removal and analysis probe employing a dual-cannula tissue removal device.

FIG. 7 illustrates an example implementation of a tissue removal and analysis probe in which the tissue removal device 210 is a variable aspiration device, such as the Nico Myriad® device. The example tissue removal device 210 includes an inner cannula 600, movable within outer cannula 610, where device 210 has sampling region 620 configured to receive a tissue sample. The tissue sample is aspirated into sampling region 620 under the application of suction (inner cannula is connectable to a suction mechanism for drawing tissue into the sampling region). Inner cannula 600 has a distal end 630 configured for cutting tissue received within sampling region.

A number of different types of tissue removal devices are currently employed. The simplest type is the use of scalpel or scissor. To enable cutting and dissection with simultaneous bipolar coagulation, electrosurgical bipolar scissors, were designed. Bipolar scissors can also be used for precise pinpoint or zone coagulation of blood-vessels and tissue. For tissue biopsy, a fine-needle might be used. During fine-needle aspiration, a long, thin needle is inserted into the suspicious area. A syringe is used to draw out fluid and cells for analysis. For a larger tissue sample, core needle biopsy might be performed. A larger needle with a cutting tip is used during core needle biopsy to draw a column of tissue out of a suspicious area. Vacuum-assisted biopsy is another type of biopsy, in which a suction device increases the amount of fluid and cells that is extracted through the needle. This can reduce the number of times the needle must be inserted to collect an adequate sample. More advanced tissue removal devices involve cutting through or vaporizing tissue using a laser such as $CO_2$, Nd:YAG and argon. The heat produced by the laser light and the penetration depth enables blood to clot quickly and minimize bleeding. It will be understood that the example embodiments described herein may be adapted to employ any one of these tissue removal devices and/or other types of tissue removal devices.

Figures 8A, 8B, 8C:
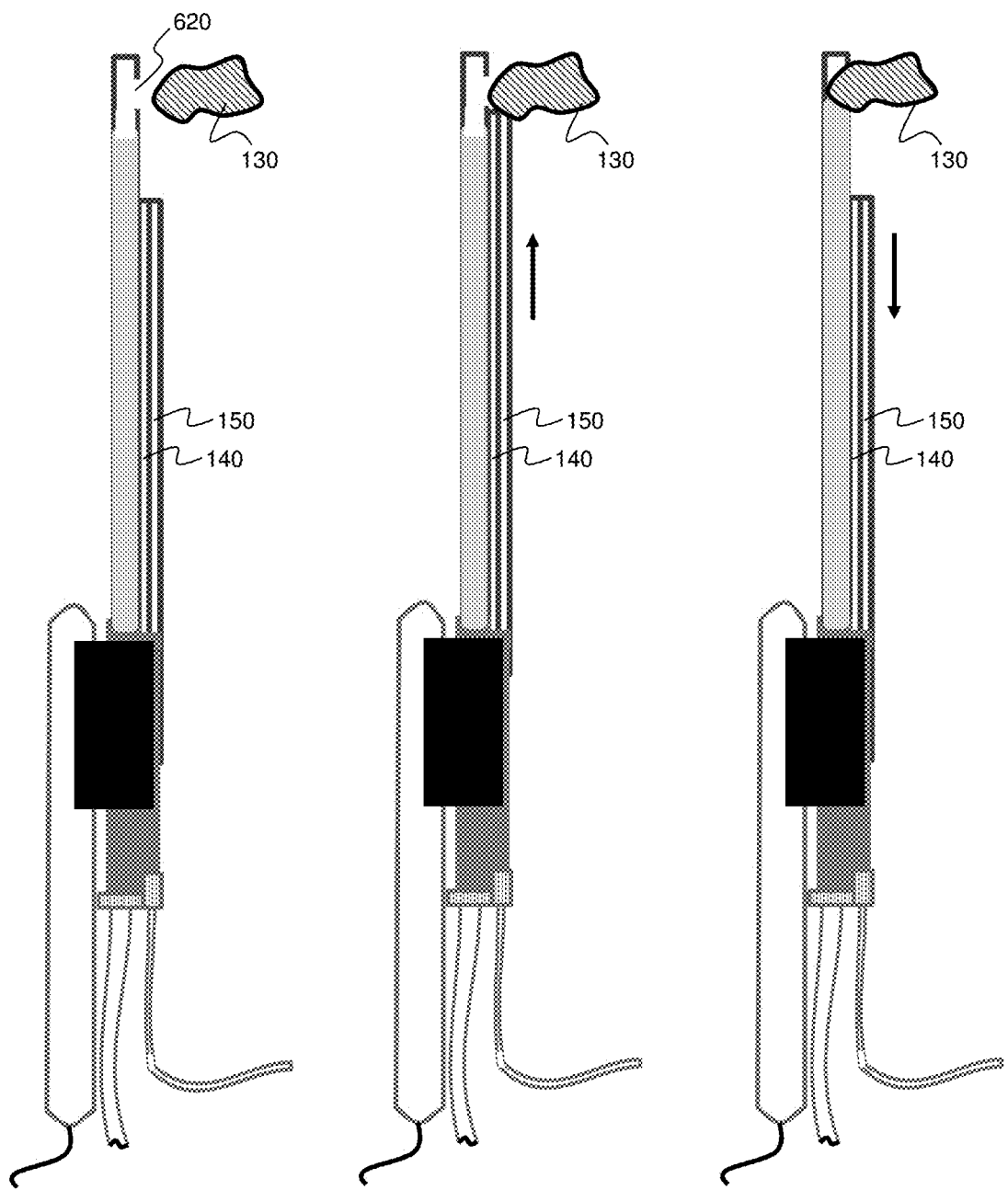
FIGS. 8A-8C illustrate the operation of an example tissue removal and analysis device having a retractable optical fiber and conduit.

FIGS. 8A-C illustrate an example tissue removal and analysis device in which the fluid conduit 150 and optical fiber 140 are positionable relative to tissue removal device. As shown in FIG. 8A, distal tissue removal portion 125 of tissue removal device may be located at or adjacent to a region of interest. Tissue may then by contacted with, or placed in front of, optical fiber 140 and conduit 150, as shown in FIG. 8B. This may be performed in the absence of suction, or, optionally, in the presence of suction. For example, suction may be controllably applied to draw the tissue into contact with the opening of the tissue removal device, thus drawing the tissue into a region that can be optically and fluidically interrogated with optical fiber 140 and fluid conduit 150, respectively, without drawing the tissue into the tissue removal device. Optical analysis may then be performed on one or more of the tissue (via light detected from optical fiber 140) and on the fluid collected in conduit 150.

The results of the optical analysis may optionally be employed to determine whether or not to perform removal (e.g. resection of biopsy) of the tissue. For example, as shown in FIG. 8C, optical fiber 140 and conduit 150 may optionally be retracted prior to performing tissue removal or sampling.

In one example implementation, a mechanism (e.g. a switch, button, or other actuation mechanism) may be employed to trigger the acquisition of optical data from optical fiber 140 and from fluid collected within fluid conduit 150. The actuation of this mechanism may also cause optical fiber 140 and conduit 150 to be moved relative to tissue removal device 120, as shown in FIG. 8B. The actuation mechanism may also be configured to move optical fiber 140 and conduit 150 forward to perform the measurement and then back to its original position (i.e. further away from the tissue removal opening) when the acquisition of optical data is complete.

In an alternative example implementation, the tissue removal and analysis device may be configured such that the tissue removal device is movable relative to optical fiber 140 and conduit 150. For example, tissue removal device 120 could be provided in an initially retracted state relative to optical fiber 140 and conduit 150, such that distal tissue removal portion 125 is retracted relative to the distal ends of optical fiber 140 and conduit 150. This would allow distal tissue regions and fluids to be optically sampled (optionally scanning a region, for example, to produce one or more images). In the event that tissue of interest is identified for sampling or resection, tissue removal device 120 can be extended such that tissue removal portion 125 is adjacent to the tissue of interest, and the tissue can be sampled or removed as described above.

Figure 9:
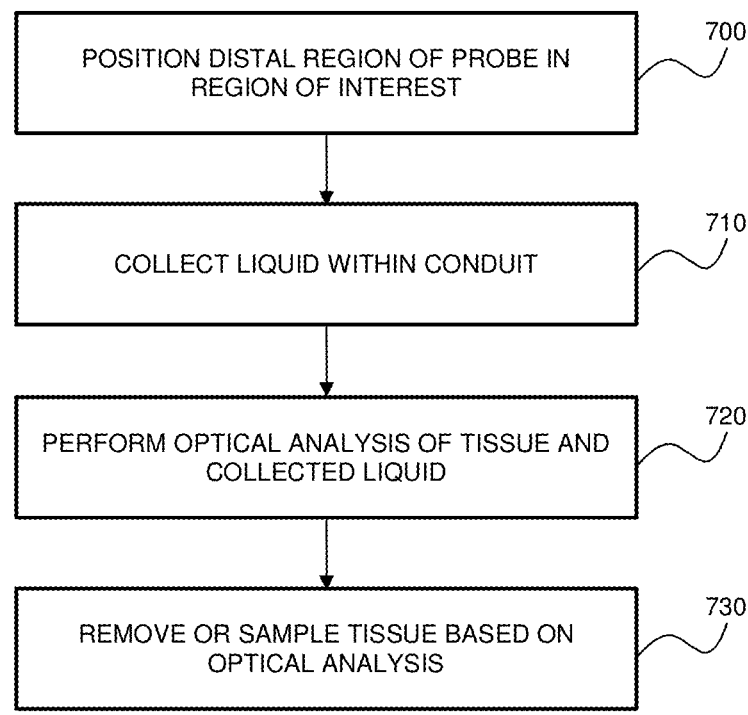
FIG. 9 is a flow chart illustrating an example method of performing optical tissue and fluid analysis followed by optional tissue removal.

FIG. 9 is a flow chart illustrating an example method of employing a tissue analysis and detection probe for the optical interrogation, and optional subsequent removal or sampling of tissue. In step 700, the distal end of the probe is placed in or adjacent to a region of interest. Fluid is then collected from the region of interest (e.g. actively, or passively, as described above), as shown at 710. The optical detection system is then employed to optically interrogate the tissue residing in the region of interest (via the solid core optical fiber) and the fluid collected within the conduit, as shown at 720. The signals produced upon optical detection are processed, and the results of the optical analysis may then be employed to determine whether or not to perform subsequent tissue removal or sampling, and if one or more criteria are met, the tissue is removed or sampled, as shown at 730.

It is noted that although the preceding disclosure has described example embodiments involving a single solid core optical fiber for sampling tissue within a region of interest and a single conduit for collecting fluid from the region of interest, it will be understood that one or more additional solid core optical fibers and/or one or more additional fluid conduits may be employed. For example, in an example implementation, a fiber bundle may be employed in place of a single optical fiber. In embodiments in which a fiber bundle is employed, one or more optical fibers may be employed for optical excitation, and one or more other optical fibers may be employed for detection. A fiber bundle may also be employed to provide spatially-resolved signals.

Figure 10:
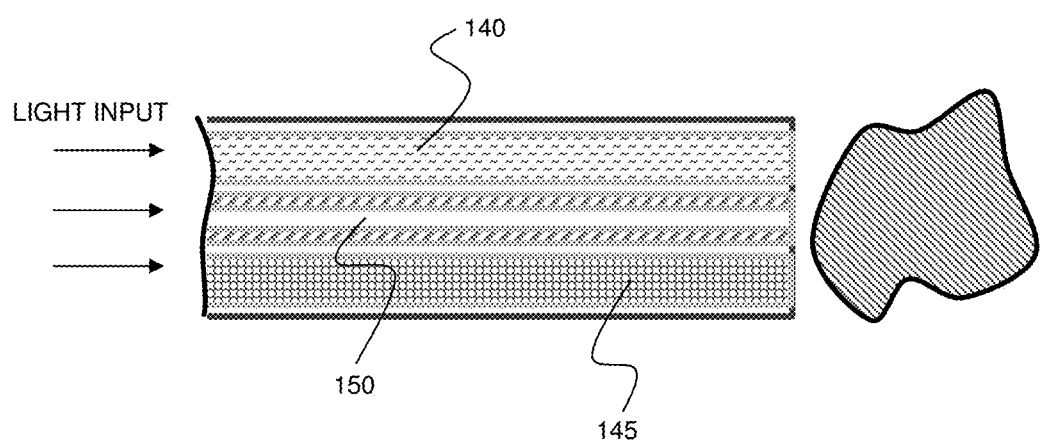
FIG. 10 shows an example configuration of the distal portion of the optical sampling component of a tissue removal and analysis probe, showing the incorporation of an additional fiber for optical coherence tomography detection.

FIG. 10 illustrates an example implementation in which an additional single mode optical fiber 145 is provided for detecting signals from the region of interest via optical coherence tomography (OCT). For example, an optical coherence detection/imaging fiber could be provided to provide additional analysis (e.g. preliminary identification) of a tumor region via high resolution optical coherence tomography (OCT). For example, Sun et al. ("Review: Optical Scanning Probe for Optical Coherence Tomography", Journal of Medical and Biological Engineering, 34(1): 95-100) describes some design of the scanning needle probes for OCT. The integrated probe, having the additional OCT modality, may provide improved accuracy of identifying tumor and tumor margins while avoiding damages to healthy tissue including fiber tracts.

Examples of the additional information one could obtain with Raman include information pertaining to cell lines, stem cells, extracellular matrix components, such as lipid, and cerebrospinal fluid. In addition, the ability to obtain Raman signals, and detect Raman signatures, from fluidic samples enables surgeons to obtain chemical information about tumors and cyst in non-solid from such as leukemia. Raman signatures obtained through cerebrospinal fluid and extracellular matrix around the tissue also provide chemical information that could help in a more accurate diagnostic of tumor tissue or tumor type around where the fluid and extracellular matrix is extracted. An example of identifying brain tumor type and grade through major and minor brain lipids can be found in reference from Krafft et al., "Near infrared Raman spectra of human brain lipids," Spectrochimica Acta Part A: Molecular and Biomolecular Spectroscopy Volume 61, Issue 7, May 2005, Pages 1529-1535.

Statistical analysis, such as principle component analysis, and discriminant analysis are commonly used to reduce the complicated Raman spectra into a few components with different variance and classifies the different Raman spectra into different categories through the similarity in the variances of the components. The accuracy of this technique typically relies on a set of controlled spectra. The more number of data (i.e. number of spectra from the different categories) and the closer the data is compared to the actual data for analysis, the higher the accuracy. For example, if this technique is used to determine between tumor and non-tumor samples, a large set of Raman spectra from tumor and non-tumor samples have to be obtained as a training set to create a classifier. In previously known devices, Raman spectra are typically only obtained from the solid tumor samples which limits most of the chemical information from the tissue itself. In stark contrast, the systems, devices and methods of the present disclosure allow Raman spectra to be obtained from both the tissue as well as from fluidics (e.g. extracellular matrix) around the tissue which enhances the chemical information obtained from the surgical area of interest. The enhanced chemical information further enables a more accurate classifier to be built; thus, increases the accurate of tumor or disease diagnostics through the use of Raman spectroscopy.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A tissue removal and optical detection probe, the probe comprising:
an elongate tissue removal device having a distal portion comprising a sampling region with an external region configured to contact a tissue sample of a patient;
an optical fiber configured to optically interrogate the tissue sample, said optical fiber having a distal end in optical communication with the external region; and
a fluid-fillable conduit having a distal aperture in fluid communication with the external region for collecting a fluid sample from the tissue sample, said optical fiber being externally spatially located from and parallel to the fluid-fillable conduit;
the fluid-fillable conduit coupled with a flow mechanism for drawing the fluid sample therein by one of passively collecting the fluid sample using a capillary action and actively collecting the fluid sample using a pumping action, the flow mechanism comprising a fluid processing device, the fluid processing device comprising a microfluidic device, the microfluidic device comprising a plurality of channels performing a plurality of distinct preprocessing functions prior to analytical interrogation, each channel of the plurality of channels having a dimension in a range of up to approximately 1 mm, the plurality of distinct preprocessing functions comprising at least two of separation, extraction, assay, and lysis, and
the fluid-fillable conduit coupled with an optical detection subsystem configured to optically interrogate the fluid sample collected in said fluid-fillable conduit,
whereby said fluid-fillable conduit forms an optical waveguide.

2. The probe of claim 1 wherein said fluid-fillable conduit comprises a hollow optical fiber.

3. The probe of claim 2, wherein said optical fiber and said fluid-fillable conduit are retractable relative to said distal portion.

4. The probe of claim 2, wherein said elongate tissue removal device comprises: a cannula having sampling region configured to receive a tissue sample at said distal portion; and a cutting mechanism associated with said cannula for cutting tissue received within said sampling region, and
wherein said cannula is configured to couple with a suction mechanism for drawing tissue into said sampling region.

5. The probe of claim 1 wherein said fluid-fillable conduit comprises a photonic crystal fiber.

6. The probe of claim 5, wherein said optical fiber and said fluid-fillable conduit are retractable relative to said distal portion.

7. The probe of claim 5, wherein said elongate tissue removal device comprises: a cannula having sampling region configured to receive a tissue sample at said distal portion; and a cutting mechanism associated with said cannula for cutting tissue received within said sampling region, and
wherein said cannula is configured to couple with a suction mechanism for drawing tissue into said sampling region.

8. The probe of claim 1, wherein said optical fiber and said fluid-fillable conduit are retractable relative to said distal portion.

9. The probe of claim 1, wherein said elongate tissue removal device comprises: a cannula having sampling region configured to receive a tissue sample at said distal portion; and a cutting mechanism associated with said cannula for cutting tissue received within said sampling region, and
wherein said cannula is configured to couple with a suction mechanism for drawing tissue into said sampling region.

10. The probe of claim 1, wherein the preprocessing function comprises lysis, wherein the lysis comprises one of mechanical lysis, electrical lysis, and ultrasonic lysis.

11. The probe of claim 1, further comprising a body portion configured to robotically support the elongate tissue removal device,
wherein the optical fiber and said fluid-fillable conduit are retractable relative to said distal portion,
wherein the elongate tissue removal device comprises:
a cannula having sampling region configured to receive a tissue sample at the distal portion; and
a cutting mechanism associated with the cannula for cutting tissue received within the sampling region, and
wherein the cannula is connectable to a suction mechanism for drawing tissue into the sampling region.

12. A method of performing tissue removal based on optical tissue analysis using a tissue removal and analysis probe, the method comprising:
providing the probe, providing the probe comprising:

providing an elongate tissue removal device having a distal portion comprising a sampling region with an external region configured to contact a tissue sample of a patient;

providing an optical fiber configured to optically interrogate the tissue sample, said optical fiber having a distal end in optical communication with the external region; and providing a fluid-fillable conduit having a distal aperture in fluid communication with the external region for collecting a fluid sample from the tissue sample, said optical fiber being externally spatially located from and parallel to the fluid-fillable conduit;

providing the fluid-fillable conduit comprising coupling the fluid-fillable conduit with a flow mechanism for drawing the fluid sample therein by one of passively collecting the fluid sample using a capillary action and actively collecting the fluid sample using a pumping action, the flow mechanism comprising a fluid processing device, the fluid processing device comprising a microfluidic device, the microfluidic device comprising a plurality of channels performing a plurality of distinct preprocessing functions prior to analytical interrogation, each channel of the plurality of channels having a dimension in a range of up to approximately 1 mm, the plurality of distinct preprocessing functions comprising at least two of separation, extraction, assay, and lysis, and providing the fluid-fillable conduit comprising coupling the fluid-fillable conduit with an optical detection subsystem configured to optically interrogate the fluid sample collected in said fluid-fillable conduit, whereby said fluid-fillable conduit forms an optical waveguide;

positioning the distal portion of the probe adjacent a tissue region;

collecting, within the fluid-fillable conduit, the fluid sample from the tissue region;

directing a first incident optical energy into the optical fiber and detecting first received optical energy responsively produced within the tissue region, thereby obtaining first received signals from the tissue sample; and directing second incident optical energy into the fluid sample collected by the fluid-fillable conduit and detecting second received optical energy responsively produced within the fluid sample, thereby obtaining second received signals from the fluid sample;

processing the first received signals from the tissue sample and the second received signals from the fluid sample to determine whether one more pre-selected criteria are met; and when the one or more criteria are satisfied, employing the tissue removal device to perform tissue removal of the patient.

13. The method of claim 12, wherein said processing comprises processing the first received signals from the tissue sample and the second received signals from the fluid sample to determine whether one or more pre-selected criteria associated with the presence of diseased tissue are met, and wherein employing the tissue removal device comprises, when the one or more preselected criteria are satisfied, employing the tissue removal device to remove diseased tissue of the patient.

14. The method of claim 12, wherein said directing the first incident optical energy into the optical fiber and detecting the first received optical energy responsively produced within the tissue region comprises directing the first incident optical energy into the optical fiber and detecting the first received optical energy responsively produced within the tissue region at a spatial location distinct from that in said directing the second incident optical energy into the fluid collected by the fluid-fillable conduit and detecting the second received optical energy responsively produced within the fluid sample.

15. The method of claim 14, further comprising determining a location of a tumor margin by using the first received signals from the tissue sample and the second received signals from the fluid sample.

16. The method of claim 12, further comprising:

determining whether one or more pre-selected criteria associated with the presence of diseased tissue are met, wherein said directing the first incident optical energy into the optical fiber and detecting the first received optical energy responsively produced within the tissue region comprises directing the first incident optical energy into the optical fiber and detecting the first received optical energy responsively produced within the tissue region at a spatially distinct location from that in said directing the second incident optical energy into the fluid collected by the fluid-fillable conduit and detecting the second received optical energy responsively produced within the fluid sample; and determining a location of a tumor margin by using the first received signals from the tissue sample and the second received signals from the fluid sample.

* * * * *